United States Patent
Drennan

(10) Patent No.: US 7,052,479 B2
(45) Date of Patent: May 30, 2006

(54) TRACTION DEVICE

(76) Inventor: Denis Burke Drennan, 4 Milburn Park, Evanston, IL (US) 60201

( * ) Notice: Subject to any disclaimer, the term of this patent is extended or adjusted under 35 U.S.C. 154(b) by 0 days.

(21) Appl. No.: 10/711,072

(22) Filed: Aug. 20, 2004

(65) Prior Publication Data

US 2006/0084898 A1  Apr. 20, 2006

(51) Int. Cl.
*A61F 5/00* (2006.01)
(52) U.S. Cl. .............. 602/32; 602/36; 602/33; 602/23
(58) Field of Classification Search ............. 602/32, 602/33, 35, 36
See application file for complete search history.

(56) References Cited

U.S. PATENT DOCUMENTS

| | | | | |
|---|---|---|---|---|
| 1,399,606 A | | 12/1921 | Ferragamo | |
| 2,696,208 A | * | 12/1954 | Falls | 602/36 |
| 2,796,061 A | * | 6/1957 | Miller | 602/33 |
| 2,817,333 A | * | 12/1957 | Cole | 602/36 |
| 2,969,790 A | * | 1/1961 | Reddig | 602/36 |
| 3,039,459 A | * | 6/1962 | Scholl | 602/36 |
| 3,385,292 A | * | 5/1968 | Hardy | 602/36 |
| 3,612,046 A | | 10/1971 | Gaylord, Jr. et al. | 128/75 |
| 3,680,551 A | | 8/1972 | Bell et al. | 128/84 R |
| 3,720,206 A | | 3/1973 | Walker et al. | 128/84 R |
| 3,728,999 A | * | 4/1973 | Thompson | 602/36 |
| 3,762,405 A | * | 10/1973 | De George | 602/23 |
| 3,771,519 A | * | 11/1973 | Haake | 602/23 |
| 3,780,731 A | * | 12/1973 | Quello | 602/36 |
| 3,804,085 A | * | 4/1974 | Eshuis et al. | 602/28 |
| 3,805,774 A | * | 4/1974 | Howard | 602/36 |
| 3,978,853 A | * | 9/1976 | Morrison | 602/36 |
| 4,181,125 A | | 1/1980 | Carlson et al. | 128/75 |
| 5,002,046 A | * | 3/1991 | Scott | 602/36 |
| 5,449,339 A | * | 9/1995 | Drennan | 602/23 |
| 5,718,669 A | * | 2/1998 | Marble | 602/5 |
| 2004/0116260 A1 | * | 6/2004 | Drennan | 482/124 |
| 2005/0131323 A1 | * | 6/2005 | Bledsoe | 602/23 |

* cited by examiner

*Primary Examiner*—Henry Bennett
*Assistant Examiner*—Amanda Wieker
(74) *Attorney, Agent, or Firm*—Gary M. Hartman; Domenica N. S. Hartman; Hartman & Hartman

(57) ABSTRACT

A traction device for applying traction to a patient's leg while supporting the patient's foot to avoid foot drop and heel or lateral malleolar pressure ulcers. The device includes a body having forefoot and lower leg portions, a continuous cavity within the forefoot and lower leg portions, and an anterior opening sized to permit a patient's foot and lower leg to pass therethrough into the cavity. The body supports the patient's lower leg so that the patient's heel is suspended within the cavity. Elements adjustably close the anterior opening and traction straps are removably attached to lateral regions of the body and extend from the forefoot portion. The interior surface of the cavity provides a sufficiently high friction interface with the patient's lower leg to prevent sliding of the body on the lower leg when full traction loads are applied through the traction straps.

20 Claims, 3 Drawing Sheets

TRACTION DEVICE

BACKGROUND OF INVENTION

1. Field of the Invention

The present invention generally relates to a traction device for an extremity of a patient. More particularly, the invention is directed to a traction device adapted to support a patient's heel and reduce heel and malleolar pressure while the patient's leg is in traction.

2. Description of the Related Art

Standard treatments of fractures of the femur include preoperative elevation on a pillow and preoperative traction. Traction typically involves skin traction by attaching to the sides of the leg a skin-tolerant device, which is then attached to a rope passing over a pulley to a weight of up to about ten pounds (about 4.5 kg or about 45 N). This type of traction is often referred to as "Buck's" traction. Skin traction devices may be applied to the skin in various ways, such as a "moleskin" held on the leg with elastic wraps. However, because of skin irritation, skin traction can typically be tolerated for only a few days until some other method (usually surgery) is used to stabilize the fracture.

Current skin traction techniques do not prevent foot drop, which is caused by relaxation and weakening of the muscles controlling the foot. Furthermore, current skin traction techniques do not elevate the heel in a manner that inhibits the development of heel or lateral malleolar pressure ulcers, to which patients with fractures of the femur are at very high risk. The incidence of such ulcers can be reduced by ensuring the transfer of pressure from the heel to the calf. Inflatable heel pressure-relieving devices are commercially available that are equipped with simple hooks on their foot portions for attachment of a traction rope. However, these devices do not provide adequate skin friction to hold the devices in place when a full traction load (e.g., about ten pounds) is applied, and therefore are inadequate to prevent heel pressure and lateral malleolar pressure. These devices also fail to provide adequate foot drop support. Also commercially available are convoluted and smooth foam traction devices that use non-removable, fixed traction straps. However, these devices do not provide means for elevating the heel to avoid heel pressure.

Various other leg traction equipment are known in the art, including U.S. Pat. No. 5,718,669 to Marble, U.S. Pat. No. 5,002,046 to Scott, U.S. Pat. No. 3,804,774 to Howard, U.S. Pat. No. 3,804,085 to Eshuis et al., and U.S. Pat. No. 3,780,731 to Quello. These patents generally disclose traction devices adapted to apply traction tension at the calf instead of the foot or ankle. Scott provides a support intended to avoid pressure sores at the heel, and Eshuis et al. disclose a boot-type device that provides support for avoiding foot-drop.

In view of the above, there remains a need for a traction device that is capable of adequately supporting the heel to avoid foot drop, relieve heel pressure to avoid heel or lateral malleolar pressure ulcers, while also being capable of transmitting full traction loads of up to ten pounds to the patient's leg.

SUMMARY OF INVENTION

The present invention provides a traction device that is capable of transmitting full traction loads of up to about ten pounds (about 45 N) to a patient's leg while supporting the patient's foot in a manner that avoids foot drop and relieves heel pressure to avoid heel or lateral malleolar pressure ulcers.

The traction device of this invention includes a body formed of a flexible and compressible material having a forefoot portion and a lower leg portion, oppositely-disposed anterior and posterior regions, oppositely-disposed lateral regions, a continuous cavity within the forefoot and lower leg portions, an interior surface within the cavity, and an anterior opening located in the anterior region and sized to permit a patient's foot and lower leg to pass therethrough into the cavity. The lower leg and forefoot portions of the body are sized and shaped to support, respectively, a patient's lower leg above a bed on which the patient reclines and the patient's foot extending in an upright position, such that the patient's heel is suspended within the cavity and heel and malleolar pressure are reduced. The patient's leg is secured within the cavity with elements adapted to adjustably close the anterior opening. The traction device further includes traction straps removably attached to the lateral regions of the body and extending from the forefoot portion of the body. According to the invention, the interior surface of the body is configured to provide a sufficiently high friction interface with the patient's lower leg to prevent sliding of the body on the patient's lower leg when the anterior opening is closed by the closing elements and a traction tension of 45 N is applied through the traction straps.

In view of the above, it can be seen that a significant advantage of this invention is that the traction device provides an improved skin contact surface for traction application, even when full traction loads are applied. The high friction interface provided by the interior surface of the body and the adjustability of the closing elements improves the ability of the traction device to stay in place to avoid frequent nursing adjustments and loss of heel, lateral malleolar, and foot drop protection. Because the traction straps are removably attached to the body, the traction device can be easily converted for use without traction to provide for full-time heel and lateral malleolar pressure protection. The device can also be used to provide foot drop support before and after femoral stabilization to avoid heel cord contracture (equinous contracture). By equipping the body with a low friction posterior surface, the effectiveness of traction can be improved as a result of reducing the amount of traction force lost to bed friction against the body of the traction device. As a result of being formed from a flexible, compressible material, the body of the traction device can be customized with a cutting instrument to protect other pressure sensitive regions of a patient's lower leg.

Other objects and advantages of this invention will be better appreciated from the following detailed description.

DETAILED DESCRIPTION

Figure 1:
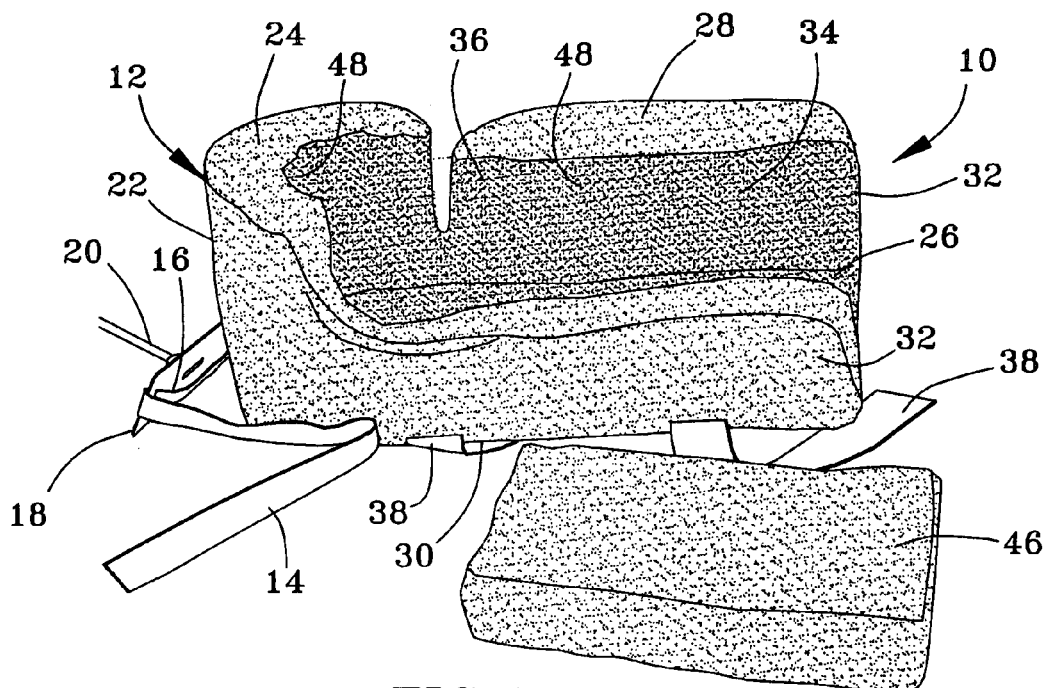
FIGS. 1 and 2 are side and end views of a traction boot in accordance with a preferred embodiment of this invention.
Figure 2:
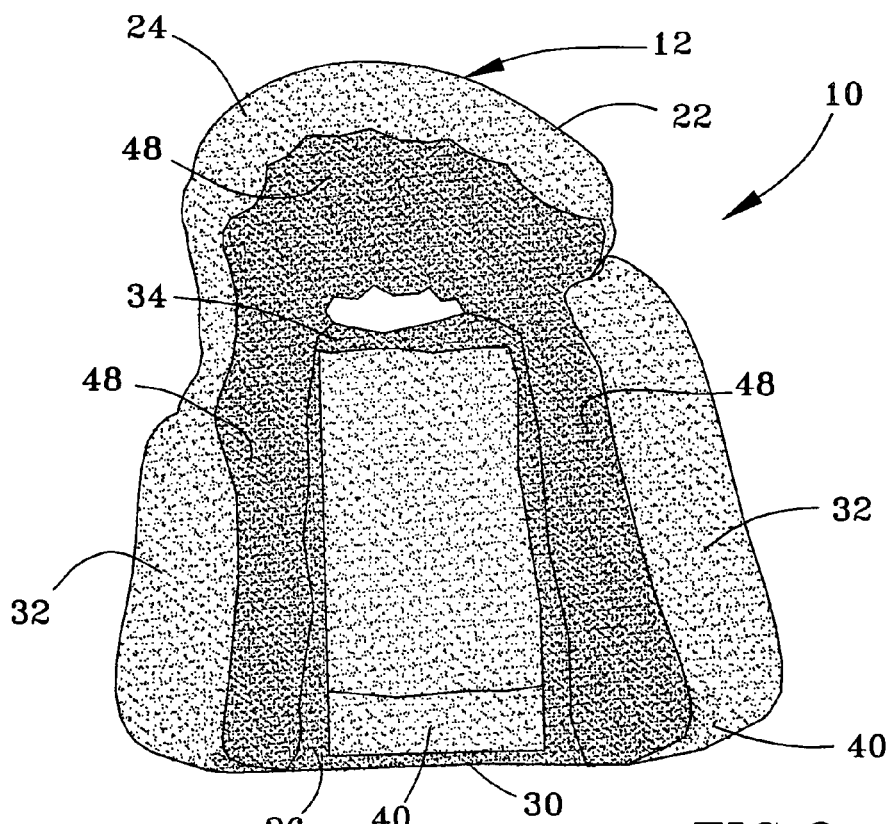

FIGS. 1 through 4 show a traction device 10 configured to be worn on a patient's foot 50 and lower leg 52 while the patient is in a generally supine position (reclining) on a bed 58 (the term "bed" is used herein to denote any surface on which a patient might recline while traction is applied to the patient's leg). The traction device 10 is configured to support the patient's heel 56 in a manner that avoids foot drop and relieves heel pressure to avoid heel or lateral malleolar pressure ulcers, while also being capable of transmitting full traction loads of up to ten pounds (about 45 N) to the patient's leg 54.

The present invention preferably makes use of a traction boot 12 that is configured similarly to a suspension boot commercially available under the name DM Systems HEELIFT®, which is disclosed in U.S. Pat. No. 5,449,339 to Drennan. The content of Drennan relating to the construction and composition of the suspension boot is incorporated herein by reference. The HEELIFT® boot is generally adapted to support the lower leg and foot of a patient with a soft foam secured to the lower leg with straps. The boot supports the lower leg and foot without applying any support pressure at the heel, thereby avoiding pressure sores at the heel. The boot has a forefoot portion that supports the foot to prevent foot-drop, and has a low friction backing and polyethylene stiffener that reduces friction against bed sheets and minimizes buckling of the boot, respectively. The boot 12 depicted in the Figures is similarly constructed and configured in accordance with Drennan, so as to benefit from its attendant features. However, the traction device 10 of this invention further includes removable traction straps 14 that run along both lateral sides of the boot 12 to form a loop 16 extending off a forefoot end 24 of the boot 12 for attachment of a traction bar 18 and rope 20. The traction straps 14 can be removed when no longer needed so that the patient can continue using the boot 12 to prevent heel pressure ulcers and foot drop.

Figure 4:
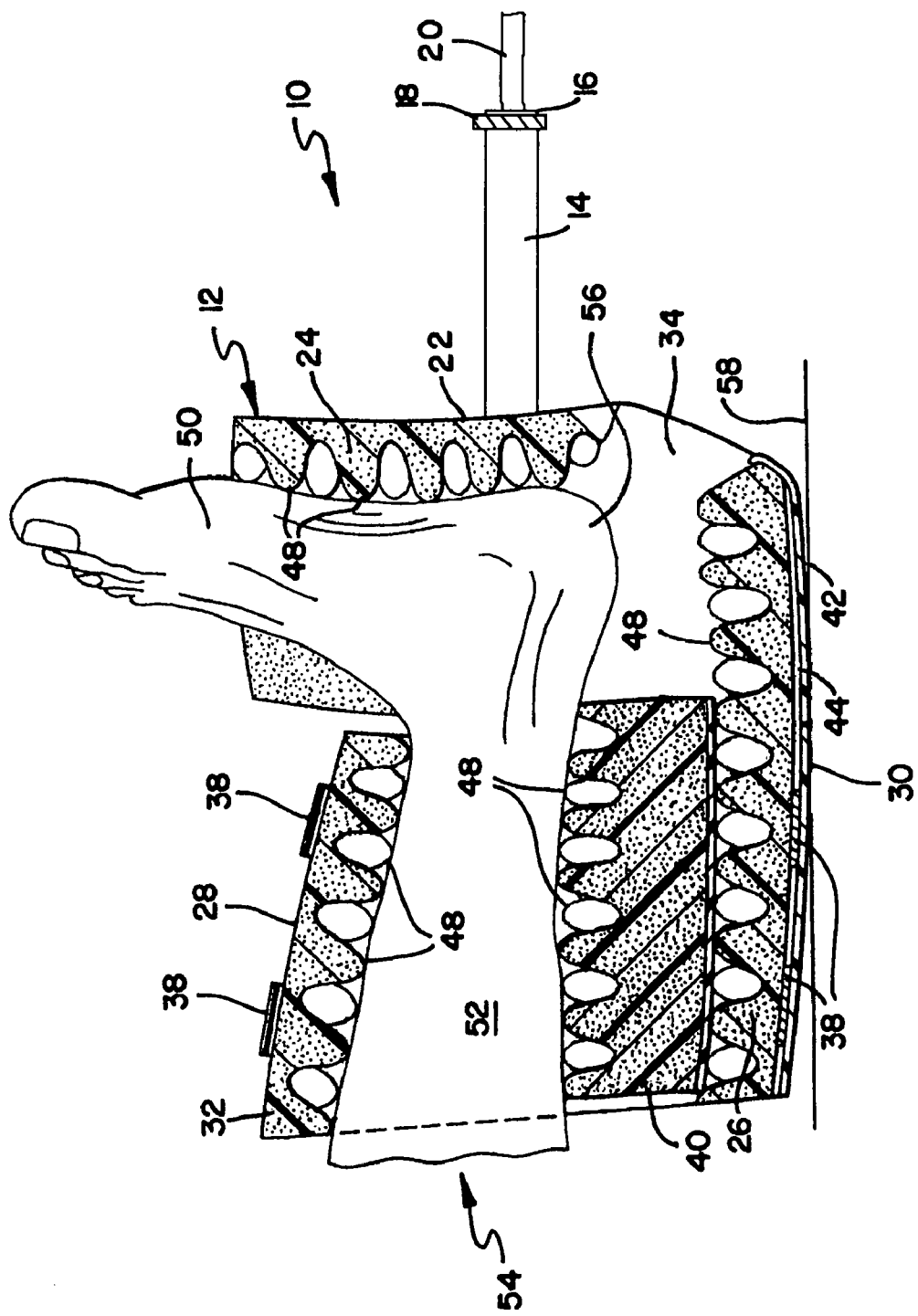
FIG. 4 represents a cross-sectional view of FIG. 3.

The traction boot 12 is shown as comprising a shell 22 having the forefoot portion 24, a lower leg portion 26, oppositely-disposed anterior and posterior regions 28 and 30, oppositely-disposed lateral regions 32, and a continuous cavity 34 within the forefoot and lower leg portions 24 and 26. An anterior opening 36 is defined by and between the lateral regions 32 in the anterior region 28, and sized to permit the patient's foot 50 and lower leg 52 to pass therethrough into the cavity 34. One of the lateral regions 32 of the shell 22 may be sized larger than the other to cover at least an anterior portion of the patient's lower leg 52. The shell 22 is secured to the lower leg 52 with straps 38 that traverse the anterior opening 36. The boot 12 further comprises a separable cushion 40 that elevates the lower leg 52 (calf), thereby supporting the foot 50 and lower leg 52 without applying any support pressure at the heel 56 to avoid pressure sores at the heel 56. The cushion 40 is shown in FIG. 4 as being secured with an adhesive to the interior surface 48 within the lower leg portion 26 of the boot 12. Alternatively, the cushion 40 could be releasably secured to the interior surface 48, such as with complementary fasteners of the hook-and-loop type, to enable removal of the cushion 40 from the boot 12. The forefoot portion 24 contacts the foot 50 and provides sufficient support to the foot 50 to prevent foot-drop (and equinous contractures). In accordance with Drennan, the boot 12 may further comprise a separable pad (not shown) that can be placed within the cavity 34 between the forefoot portion 24 and the patient's foot 50 to provide additional support.

Figure 3:
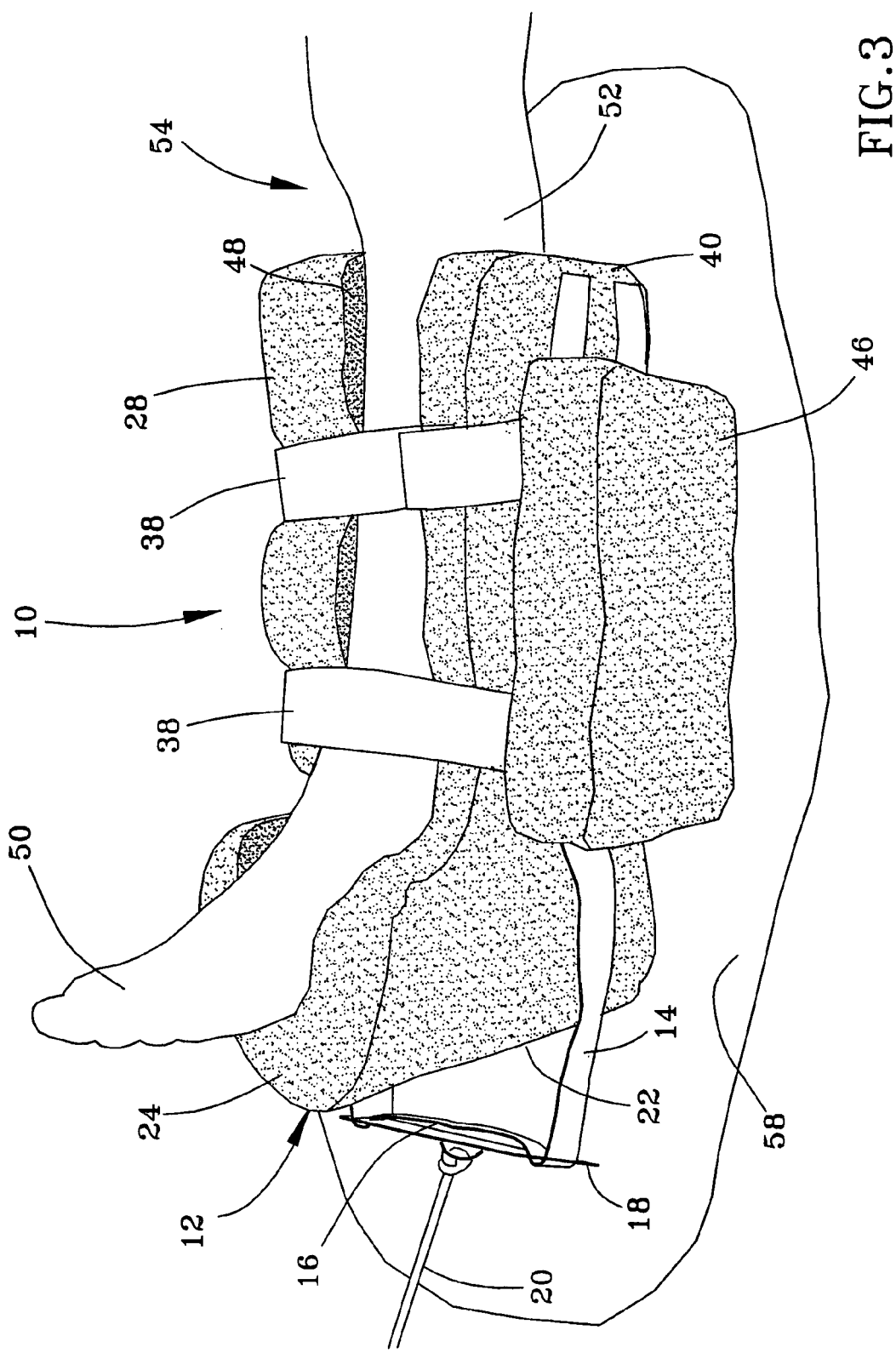
FIG. 3 depicts the traction boot of FIGS. 1 and 2 as it appears when worn on the lower leg of a patient.

As can be seen in FIG. 4, the boot 12 may include a low-friction backing 42 on its posterior region 30 to reduce friction with bed sheets, which would have the effect of reducing the effectiveness of traction. The low-friction backing 42 preferably overlies a stiffener 44 that minimizes buckling of the boot 12 between the forefoot and lower leg portions 24 and 26. Suitable materials for the low-friction backing 42 and stiffener 44 include a tricot material and polyethylene, respectively. FIGS. 1 and 3 further show the traction device 10 as being equipped with a pad 46 that can be placed adjacent the lateral regions 32 of the boot 12 to control external rotation during traction and after traction is removed. The pad 46 is preferably releasably attached to one of the lateral regions 32 with adhesive, though hook-and-loop fasteners could also be used.

The shell 22 is preferably a unitary body formed of a flexible, compressible foam material. A particularly preferred shell 22 is formed from a slab of open-cell non-allergenic resilient foam material such as polyurethane foam, with sufficient thickness to elevate the patient's foot 50 and provide sufficient structural support to inhibit movement of the foot 50 and lower leg 52. The shell 22 has a soft foam interior surface 48 that provides a high friction interface with the patient's skin. In particular, the interior surface 48 provides an improved skin contact surface for traction over prior art heel pressure-relieving devices. As depicted in the Figures, the interior surface 48 is smooth, though alternatively the surface 48 could be convoluted, having a pattern of peaks and valleys. Commercially available foam materials having this type of surface are known as convoluted foam or egg carton foam. In combination with the adjustable straps 38, which are preferably closed with a hook-and-loop type fastener, the soft foam interior surface 48 is able to prevent sliding of the boot 12 down the lower leg 52 when a full traction tension (e.g., ten pounds or more) is applied through the traction straps 14.

The removable traction straps 14 of the traction device 10 are preferably secured to the lateral regions 32 of the boot 12 with complementary fasteners of the hook-and-loop type, which enable the traction straps 14 to be selectively attached and removed from the boot 12. As such, the traction straps 14 can be removed when traction is no longer needed, while allowing the patient to continue wearing the boot 12 to prevent heel pressure ulcers and foot drop. The loop 16 formed by the traction straps 14 preferably extends off the forefoot portion 24 a distance of about four inches (about ten cm). The loop 16 is routed through the traction bar 18, which is attached to the traction rope 20. The rope 20 can then be passed through a pulley (not shown) and attached to a weight (not shown) to apply the traction load.

In view of the above, the present invention provides a traction device 10 better capable of staying in place to avoid frequent nursing adjustments and loss of heel, lateral malleolar, and foot drop protection. Foot drop sup-port can be provided with the device 10 before and after femoral stabilization to avoid heel cord contracture (equinous contracture). The low-friction backing 42 improves the effectiveness of traction as there is much less force being reduced by bed sheet friction in comparison to the foam construction of the boot shell 22. In addition, the traction device 10 can be easily converted for fulltime heel and lateral malleolar pressure protection. Because of its soft foam construction, the boot 12 can be customized by shaping with scissors to protect any pressure sensitive region on the lower leg.

While the invention has been described in terms of a preferred embodiment, it is apparent that other forms could be adopted by one skilled in the art. For example, the physical configuration of the boot 12 could differ from that shown, and materials other than those noted could be use. Therefore, the scope of the invention is to be limited only by the following claims.

The invention claimed is:

1. A traction device comprising:
   a body formed of a flexible and compressible material having a forefoot portion and a lower leg portion, oppositely-disposed anterior and posterior regions, oppositely-disposed lateral regions, a continuous cavity within the forefoot and lower leg portions, an interior surface within the cavity, and an anterior opening located in the anterior region and sized to permit a patient's foot and lower leg to pass therethrough into the cavity, the cavity within the lower leg and forefoot portions being sized and shaped to support respectively a patient's lower leg above a bed on which the patient reclines and the patient's foot extending in an upright position and so that the patient's heel is suspended within the cavity and heel and malleolar pressure are reduced;
   means for adjustably closing the anterior opening;
   traction straps extending from the forefoot portion of the body; and
   means for removably attaching the traction straps to the lateral regions of the body and for enabling the traction straps to be detached from the body while the patient's lower leg and foot remain supported by and within the body;
   wherein the interior surface of the body provides a sufficiently high friction interface with the patient's lower leg to prevent sliding of the body on the patient's lower leg when the anterior opening is closed by the closing means and a traction tension of 45 N is applied through the traction straps.

2. The traction device according to claim 1, wherein the traction straps define a loop.

3. The traction device according to claim 2, further comprising a traction bar secured to the loop of the traction straps.

4. The traction device according to claim 3, further comprising a traction rope secured to the traction bar.

5. The traction device according to claim 1, wherein the adjustable closing means comprises straps releasably attached to the lateral regions of the body.

6. The traction device according to claim 1, wherein one of the lateral regions of the body is larger than the other of the lateral regions and is sufficiently sized to cover at least an anterior portion of the patient's lower leg.

7. The traction device according to claim 1, further comprising means for reducing friction on the posterior region of the body to promote sliding movement of the body on the bed on which the patient reclines.

8. The traction device according to claim 1, further comprising means for stiffening the posterior region of the body to inhibit buckling of the body between the forefoot and lower leg portions thereof.

9. The traction device according to claim 1, further comprising a separate support cushion within the cavity of the body, the support cushion being located within the lower leg portion of the body for supporting the patient's lower leg within the cavity and suspending the patient's heel within the cavity.

10. The traction device according to claim 9, wherein the support cushion is formed of a flexible and compressible material.

11. The traction device according to claim 9, further comprising means for securing the support cushion to the interior surface within the lower leg portion of the body.

12. The traction device according to claim 1, further comprising a separate support pad and means for releasably securing the support pad to one of the lateral regions of the body to inhibit rolling of the patient's lower leg.

13. A traction device comprising:
   a unitary body formed of a flexible, compressible foam material having integral forefoot and lower leg portions, oppositely-disposed anterior and posterior regions, oppositely-disposed lateral regions, a continuous cavity within the forefoot and lower leg portions, an interior surface within the cavity, and an anterior opening located in the anterior region and sized to permit a patient's foot and lower leg to pass therethrough into the cavity, the cavity within the lower leg and forefoot portions being sized and shaped to support respectively a patient's lower leg above a bed on which the patient reclines and the patient's foot extending in an upright position;
   means for adjustably closing the anterior opening;
   traction straps extending from the forefoot portion of the body;
   complementary fastening means for removably attaching the traction straps to the lateral regions of the body and for enabling the traction straps to be detached from the body while the patient's lower leg and foot remain supported by and within the body;
   means for reducing friction on the posterior region of the body to promote sliding movement of the boot on the bed on which the patient reclines;
   means for stiffening the posterior region of the body to inhibit buckling of the boot between the forefoot and lower leg portions thereof; and
   a support cushion within the cavity of the body, the support cushion being located within the lower leg portion of the body for supporting the patient's lower leg within the cavity and suspending the patient's heel within the cavity so that heel and malleolar pressure are substantially absent;
   wherein the interior surface of the body provides a sufficiently high friction interface with the patient's lower leg to prevent sliding of the body on the patient's lower leg when the anterior opening is closed by the closing means and a traction tension of 45 N is applied through the traction straps.

14. The traction device according to claim 13, wherein the traction straps define a loop.

15. The traction device according to claim 14, further comprising a traction bar secured to the loop of the traction straps.

16. The traction device according to claim 15, further comprising a traction rope secured to the traction bar.

17. The traction device according to claim 13, wherein the adjustable closing means comprises straps releasably attached to the lateral regions of the body.

18. The traction device according to claim 13, wherein one of the lateral regions of the body is larger than the other of the lateral regions and is sufficiently sized to cover at least an anterior portion of the patient's lower leg.

19. The traction device according to claim 13, wherein the support cushion is formed of a flexible, compressible foam material.

20. The traction device according to claim 13, further comprising a support pad and means for releasably securing the support pad to one of the lateral regions of the body to inhibit rolling of the patient's lower leg.

* * * * *